United States Patent [19]

Brobyn et al.

[11] Patent Number: 5,209,921
[45] Date of Patent: May 11, 1993

[54] AEROSOL COMPOSITIONS

[75] Inventors: Susan E. Brobyn; Robert D. Mackie, both of Weybridge, England

[73] Assignee: Beecham Group plc, United Kingdom

[21] Appl. No.: 852,347

[22] Filed: Mar. 17, 1992

Related U.S. Application Data

[63] Continuation of Ser. No. 525,330, May 17, 1990, abandoned.

[30] Foreign Application Priority Data

May 19, 1989 [GB] United Kingdom ............. 8911529
Nov. 13, 1989 [GB] United Kingdom ............. 8925605

[51] Int. Cl.$^5$ .............................................. A61L 9/04
[52] U.S. Cl. .................................. 424/45; 424/43; 424/47
[58] Field of Search .......................... 424/43, 45, 47

[56] References Cited

U.S. PATENT DOCUMENTS

| | | | |
|---|---|---|---|
| 3,912,667 | 10/1975 | Spitzer et al. | 260/2.5 |
| 4,134,968 | 1/1979 | Stebles | 424/47 |
| 4,243,548 | 1/1981 | Heeb et al. | 252/305 |
| 4,450,151 | 5/1984 | Shinozawa | 424/46 |
| 4,716,032 | 12/1987 | Westfall et al. | 424/45 |

FOREIGN PATENT DOCUMENTS 413488 12/1966 Switzerland.
634480 2/1983 Switzerland.
1099722 1/1968 United Kingdom.

OTHER PUBLICATIONS

Patent Abstracts of Japan, vol. 11, No. 214 (C-434) (2661), 1987.
Patent Abstracts of Japan, vol. 6, No. 11 (C-88) (889), 1982.
Patent Abstracts of Japan, vol. 11, No. 206 (C-433) (2653), 1987.
Chemie-Lexikon, 8th Edition, vol. 4, p. 2579, 1985.
Seifen-Ole-Fette-Wachse, vol. 111, pp. 179-180, 1985.

Primary Examiner—Thurman K. Page
Assistant Examiner—W. Benston
Attorney, Agent, or Firm—Rosenman & Colin

[57] ABSTRACT

Aerosol compositions for topical application, conferring a cooling effect on the body and suitable for use in the alleviation of pain, such as muscular or rheumatic pain, which compositions do not contain environmentally unacceptable chlorofluorocarbons but satisfy safety guidelines on flammability, and comprise an organic substance, other than a chlorofluorocarbon, having a boiling point within the range of from 10° to 40° C. and an organic substance, other than a chlorofluorocarbon, having a boiling point within the range of from −45° to −10° C., in a ratio of from 3 to 7 parts by weight of the higher boiling component (serving primarily as a coolant) per part by weight of the lower boiling component (serving primarily as a propellant).

14 Claims, No Drawings

AEROSOL COMPOSITIONS

This application is a continuation of Ser. No. 07/525,330, filed May 17, 1990 now abandoned.

The present invention relates to a composition suitable for use as a so-called aerosol "freeze spray"

So-called "freeze sprays" are aerosol compositions which, when sprayed onto a patient's skin, have a cooling or "freezing" effect on that part of the body. They are used in the alleviation of, for example, muscular pain, rheumatic pain, lumbago, sciatica, and neuritis. Such freeze sprays currently comprise a high proportion of, or in some cases consist entirely of, chlorofluorocarbons (CFC's).

There has recently been considerable concern about the use of chlorofluorocarbons, and their contribution to pollution of the environment and, in particular, their effect in causing depletion of the ozone layer in the upper atmosphere. There has therefore been considerable effort made to reduce the use of chlorofluorocarbons in, inter alia, aerosol compositions by the use of alternative propellants and other components.

Considerable advancement has been made toward reducing or eliminating the use of chlorofluorocarbons in many types of aerosol composition, but, despite considerable effort in that direction, it has not hitherto been possible to find alternative components suitable for use in freeze sprays. This is because the chlorofluorocarbons themselves are largely responsible for the freezing effect on the skin and also have the useful property of being good solvents. The alternative propellants that are typically being used in other aerosol compositions, such as butane, pentane, propane and nitrogen generally do not have both of these desirable properties.

Another factor that has to be borne in mind is the safety of aerosol sprays and, in particular, their flammability. One advantage of chlorofluorocarbons as aerosol propellants has been their non-flammability, and one disadvantage of the alternative propellants, such as butane and propane, has been their flammability. One method of measuring flammability of aerosol sprays is the so-called "flame extension" method, in which an aerosol is sprayed sideways into a candle flame at a distance of 150 mm from the flame, and the resulting side extension of the flame is measured. According to the industry guidelines issued by the British Aerosol Manufacturers Association (BAMA), the flame extension should not exceed 450 mm.

There has therefore been a desire to produce an aerosol freeze spray which avoids the use of chlorofluorocarbons and satisfies the safety guidelines on flammability.

The present invention now provides an aerosol composition comprising:
 (i) an organic substance, other than a chlorofluorocarbon, having a boiling point within the range of from 10° C. to 40° C., and
 (ii) an organic substance, other than a chlorofluorocarbon, having a boiling point within the range of from −45° C. to −10° C., or having a vapour pressure within the range of from 15 to 115 psig (pounds per square inch; at 20° C.); in a ratio of from 2.5 to 6 parts by volume of component (i) per 1 part by volume of component (ii) (or from 3 to 7 parts by weight of component (i) per 1 part by weight of component (ii)).

Such a composition avoids the use of chlorofluorocarbons and has been found to have a good freeze-cooling effect on the patient's skin while still satisfying the safety guidelines regarding flammability.

Component (i) is an organic substance, other than a chlorofluorocarbon, having a boiling point within the range of from 10° C. to 40° C., preferably from 20° C. to 35° C., especially from 25° C. to 35° C.. This component serves primarily as a coolant.

A preferred substance suitable for use as component (i) is isopentane (2-methylbutane; boiling point approx. 28° C.). Other suitable substances include, for example, n-pentane (boiling point 36° C.), diethyl ether (ethoxyethane; boiling point 35° C.), and methylene chloride (boiling point 40° C.). Two or more such substances may be used together as component (i).

Component (ii) is an organic substance, other than a chlorofluorocarbon, having a boiling point within the range of from −45° C. to −10° C., preferably from −30° C. to −20° C., especially from −26° C. to −20° C., or having a vapour pressure (at 20° C.) within the range of from 15 to 115 psig, preferably from 30 to 65 psig, especially from 55 to 65 psig. This component serves primarily as a propellant.

A preferred substance for use as component (ii) is dimethyl ether (methoxymethane; boiling point −250° C.). Other suitable substances include, for example, partially hydrogenated chlorofluorocarbons, e.g. HCFC-22, and hydrocarbons, e.g. butane/propane blends. Two or more such substances may be used together as component (ii).

Components (i) and (ii) are used in a ratio (ii):(i) of from 1:2.5 to 1:6 by volume, or from 1:3 to 1:7 by weight; preferably from 1:3 to 1:5.5 by volume, or from 1:3 to 1:5 by weight; for example from 1:3 to 1:4 by volume or 1:3 to 1:4 by weight, or from 1:4 to 1:5 by volume or 1:4 to 1:5 by weight.

Components (i) and (ii) together suitably comprise from 65% to 100% by weight of the total aerosol composition. Components (i) and (ii) together suitably comprise from 65% to 100% by volume of the total aerosol composition.

The aerosol composition according to the invention may additionally comprise a pharmaceutically active substance. Examples of suitable such substances include a topical analgesic agent, for example, salicylic acid, a salicylic acid ester, acetylsalicylic acid (aspirin), ibuprofen, indomethacin, or, preferably, glycol salicylate; an anti-inflammatory agent, for example a corticosteroid, e.g. hydrocortisone; a local anaesthetic agent; and an anti-histamine agent.

Such a pharmaceutically active substance may suitably be present in an amount of up to 15% by volume, or up to 20% by weight, based on the total composition.

The pharmaceutically active substance should preferably be dissolved in the mixture of components (i) and (ii) to give a single-phase mixture. It has been found that, when using, say, glycol salicylate as an analgesic agent, the use of dimethyl ether as the propellant has the advantage of aiding solubilisation of the analgesic agent, whereas isopentane and glycol salicylate alone give a two-phase mixture. The use of other propellants, such as butane, does not have this advantage.

The aerosol composition according to the invention may also comprise an organic solvent, in addition to any organic solvent in component (i) or (ii), suitably in an amount of up to 35% by volume, or up to 35% by weight. Examples of suitable organic solvents include isopropanol and ethanol. While it is by no means an essential component, the presence of an organic solvent can also assist in achieving solubilisation of any pharmaceutically active substances present. In the absence of an organic solvent, it may be necessary, in some circumstances, to increase the proportion of either component (i) or (ii), or both, in order to achieve the desired solubilisation.

The aerosol composition according to the invention may furthermore comprise one or more auxiliary components, for example a perfume or fragrance (e.g. menthol), suitably in an amount of up to 5%, preferably up to 2%, by weight or by volume.

The aerosol composition according to the invention is most suitably discharged from an aerosol container at a discharge rate of from 0.2 to 3.5 g/sec, preferably from 0.2 to 1.0 g/sec, such as from 0.2 to 0.5 g/sec or from 0.45 to 0.85 g/sec. The desired discharge rate can be achieved by suitable choice of valve size within the aerosol spray mechanism in a manner known per se.

Changes in the proportions of coolant and propellant within the composition will also affect the discharge rate, in that a higher proportion of propellant will result in an increased vapour pressure within the aerosol container, and may induce a higher discharge rate.

These factors can readily be varied by a person skilled in the art, who can readily choose a combination of coolant:propellant ratio and valve size to give a discharge rate such that flammability safety requirements are satisfied.

Aerosol containers often have both a liquid-phase tap and a vapour-phase tap, that is to say, one outlet extending into the liquid phase within the container (usually a tube extending to the base of the container) and one outlet from the vapour phase at the top of the container. It has, however, been found advantageous for the aerosol composition according to the present invention to be dispensed from a container having only a liquid-phase tap. This has been found to have two advantages: first, it reduces consumption of the propellant and thus enables a smaller proportion of that component to be used; and secondly, it results in a less diffuse, heavier, spray, which in turn gives an improved cooling effect on the skin.

The following Examples 1–7 illustrate the present invention.

The components listed in each example were mixed in the proportions shown and filled into an aerosol container in a conventional manner

EXAMPLE 1

| | % w/w | |
|---|---|---|
| isopentane | 60.06 | (84.03 ml) |
| dimethyl ether | 19.71 | (25.64 ml) |
| isopropanol | 9.18 | (10.21 ml) |
| glycol salicylate | 9.89 | (9.89 ml) |
| menthol | 1.15 | (1.0 g) |

The composition of Example 1 was prepared by mixing together the quantities shown in parenthesis. When discharged from an aerosol container at a discharge rate of about 0.35 g/sec, it gave a flame extension (determined as specified above) not exceeding 450 nm.

EXAMPLE 2

| | % w/w |
|---|---|
| isopentane | 84.60 |
| dimethyl ether | 15.40 |

EXAMPLE 3

| | % w/w |
|---|---|
| isopentane | 60.72 |
| dimethyl ether | 20.06 |
| isopropanol | 9.22 |
| methyl salicylate | 10.00 |

EXAMPLE 4

| | % w/w |
|---|---|
| isopentane | 46.62 |
| dimethyl ether | 18.61 |
| ethanol | 33.27 |
| methanol | 0.50 |
| indomethacin | 1.0 |

EXAMPLE 5

| | % w/w |
|---|---|
| isopentane | 60.91 |
| dimethyl ether | 27.69 |
| ethanol | 8.32 |
| methanol | 0.50 |
| glycol salicylate | 8.58 |

EXAMPLE 6

| | % w/w |
|---|---|
| isopentane | 65.54 |
| dimethyl ether | 16.92 |
| isopropanol | 7.96 |
| glycol salicylate | 8.58 |
| menthol | 1.00 |

EXAMPLE 7

| | % w/w |
|---|---|
| isopentane | 67.77 |
| dimethyl ether | 14.41 |
| isopropanol | 6.82 |
| glycol salicylate | 10.00 |
| menthol | 1.00 |

When the compositions of Examples 6 and 7 were discharged from an aerosol container at a discharge rate of about 0.75 g/sec, each gave a flame extension (determined as specified above) not exceeding 450 mm.

What is claimed is:
1. An aerosol composition comprising:
   (i) isopentane, n-pentane, diethyl ether or methylene chloride, or mixtures of any two or more thereof having a boiling point within the range of from 10° C. to 40° C., and

(ii) dimethyl ether, a hydrocarbon or a partially hydrogenated chlorofluorocarbon, or mixture of any two or more thereof having a boiling point within the range of from −45° C. to −10° C., or having a vapor pressure within the range of from 15 to 115 psig (pounds per square inch; at 20° C.);

in a ratio of from 2.5 to 6 parts by volume of component (i) per 1 part by volume of component (ii) (or from 3 to 7 parts by weight of component (i) per 1 part by weight of component (ii)).

2. A composition according to claim 1 wherein components (i) and (ii) are present in a ratio (ii):(i) of from 1:3 to 1:5.5 by volume or from 1:3 to 1:4 by weight.

3. A composition according to claim 1 wherein the ratio (ii):(i) is from 1:4 to 1:5 by volume or 1:4 to 1:5 by weight.

4. A composition according to claim 1 wherein components (i) and (ii) together comprise from 65 to 100% by weight or from 65 to 100% by volume of the total aerosol composition.

5. A pharmaceutical composition for topical application to the skin comprising a substance that is pharmaceutically active when topically applied to the skin in an amount up to 15% by volume or up to 20% by weight of the total composition, and
   (i) an organic substance, other than a chlorofluorocarbon, having a boiling point within the range of from 10° C. to 40° C., and
   (ii) an organic substance, other than a chlorofluorocarbon, having a boiling point within the range of from −45° to −10° C., or having a vapor pressure within the range of from 15 to 115 psig (pounds per square inch; at 20° C.);

in a ratio of from 2.5 to 6 parts by volume of component (i) per 1 part by volume of component (ii) (or from 3 to 7 parts by weight of component (i) per 1 part by weight of component (ii)).

6. A composition according to claim 5 wherein the pharmaceutically active substance is a topical analgesic agent, an anti-inflammatory agent, a local anaesthetic agent or an anti-histamine agent.

7. A composition according to claim 6 wherein the pharmaceutically active substance is salicylic acid or an ester thereof, acetyl salicylic acid, glycol salicylate, ibuprofen, indomethacin, or hydrocortisone.

8. A composition according to claim 1 further comprising an organic solvent in addition to any organic solvent in component (i) or (ii) in an amount up to 35% by volume or up to 35% by weight of the total composition.

9. A composition according to claim 8 containing isopropanol or ethanol as the said organic solvent.

10. A composition according to claim 1 further comprising a perfume in an amount up to 5% by weight or volume of the total composition.

11. A composition according to claim 10 wherein the perfume is menthol.

12. An aerosol container containing a composition as defined in claim 1 having a discharge rate of from 0.2 to 3.5 g/sec.

13. An aerosol container as defined in claim 12 having only a liquid-phase tap.

14. An aerosol composition comprising 67.77% by weight of isopentane, 14.41% by weight of dimethylether, 6.82% by weight of isopropanol, 10.00% by weight of glycol salicylate, and 1.00% by weight of menthol.

* * * * *